United States Patent
Kim et al.

(10) Patent No.: US 9,683,114 B2
(45) Date of Patent: Jun. 20, 2017

(54) MONOMER FOR HARDMASK COMPOSITION, HARDMASK COMPOSITION INCLUDING THE MONOMER, AND METHOD OF FORMING PATTERNS USING THE HARDMASK COMPOSITION

(71) Applicant: SAMSUNG SDI CO., LTD., Yongin-si, Gyeonggi-do (KR)

(72) Inventors: Hea-Jung Kim, Suwon-si (KR); Sung-Hwan Kim, Suwon-si (KR); Youn-Hee Nam, Suwon-si (KR); Yun-Jun Kim, Suwon-si (KR); Joon-Young Moon, Suwon-si (KR); Hyun-Ji Song, Suwon-si (KR); Yong-Woon Yoon, Suwon-si (KR); Chung-Heon Lee, Suwon-si (KR)

(73) Assignee: SAMSUNG SDI CO., LTD., Yongin-Si, Gyeonggi-Do (KR)

( * ) Notice: Subject to any disclaimer, the term of this patent is extended or adjusted under 35 U.S.C. 154(b) by 0 days.

(21) Appl. No.: 14/609,824

(22) Filed: Jan. 30, 2015

(65) Prior Publication Data
US 2015/0268558 A1  Sep. 24, 2015

(30) Foreign Application Priority Data
Mar. 19, 2014 (KR) .......... 10-2014-0032392

(51) Int. Cl.
G03F 7/004 (2006.01)
G03F 7/09 (2006.01)
C07C 251/24 (2006.01)
C07C 233/80 (2006.01)
C09D 7/12 (2006.01)
G03F 7/075 (2006.01)

(52) U.S. Cl.
CPC .......... *C09D 7/1233* (2013.01); *C07C 233/80* (2013.01); *C07C 251/24* (2013.01); *G03F 7/0752* (2013.01); *G03F 7/094* (2013.01); *C07C 2103/18* (2013.01); *C07C 2103/24* (2013.01); *C07C 2103/50* (2013.01)

(58) Field of Classification Search
None
See application file for complete search history.

(56) References Cited

U.S. PATENT DOCUMENTS

| | | | | |
|---|---|---|---|---|
| 2,868,799 A * | 1/1959 | Neeff | ......... | C09B 1/00 548/149 |
| 3,368,974 A * | 2/1968 | Sparks | ......... | C08K 5/29 252/401 |
| 3,763,107 A * | 10/1973 | D'Alelio | ......... | C08G 73/18 524/597 |
| 7,632,622 B2 * | 12/2009 | Uh | ......... | G03F 7/0387 430/270.1 |
| 9,348,229 B2 * | 5/2016 | Nam | ......... | H01L 21/3081 |
| 2003/0143480 A1 * | 7/2003 | Ueda | ......... | C08G 73/22 430/192 |
| 2003/0176623 A1 * | 9/2003 | Lowack | ......... | C08G 73/00 528/210 |
| 2004/0026663 A1 * | 2/2004 | Heuer | ......... | C07F 15/0033 252/301.16 |
| 2004/0082756 A1 * | 4/2004 | Sezi | ......... | C08G 69/26 528/363 |
| 2007/0003863 A1 * | 1/2007 | Uh | ......... | G03F 7/091 430/270.1 |
| 2008/0044664 A1 * | 2/2008 | Shirato | ......... | C08G 73/22 428/426 |
| 2013/0087529 A1 * | 4/2013 | Hatakeyama | ....... | H01L 21/0271 216/47 |
| 2013/0324662 A1 * | 12/2013 | Honda | ......... | C09D 179/04 524/595 |
| 2015/0187589 A1 * | 7/2015 | Nam | ......... | H01L 21/3081 438/703 |
| 2015/0301446 A1 * | 10/2015 | Shin | ......... | C07C 63/15 216/47 |

FOREIGN PATENT DOCUMENTS

| | | |
|---|---|---|
| CN | 1472195 A | 2/2004 |
| CN | 101198907 A | 6/2008 |
| CN | 102227458 A | 10/2011 |
| JP | 03-192264 * | 8/1991 |
| JP | 05-281551 * | 10/1993 |
| JP | 5-281551 A | 10/1993 |
| KR | 10-2005-0033443 A | 4/2005 |
| KR | 10-0874655 B1 | 12/2008 |

(Continued)

OTHER PUBLICATIONS

Zadrozna et al. "Novel Optical material: Polyarylates with azomethine side-chain groups", J. Appl. Poly. Sci., vol. 80 pp. 1374-1382 (2001).*
Kaya et al,, "Synthesis and charachterization of fluorescent . . . ", RTeact. Funct. Polymer., vol. 70 pp. 815-826 (2010).*
Taneda et al. "Vapor switching of photochormism . . . " Chem. Lett., vol. 36(3) pp. 354-355 (2007).*
Kane et al., "Synthesis of N-substituted polybenzimidazoles by . . . " Poly. Preprint (1991) pp. 232-233.*

(Continued)

*Primary Examiner* — Martin Angebranndt
(74) *Attorney, Agent, or Firm* — Lee & Morse, P.C.

(57) ABSTRACT

A monomer for a hardmask composition, a hardmask composition, and a method of forming patterns, the monomer being represented by the following Chemical Formula 1:

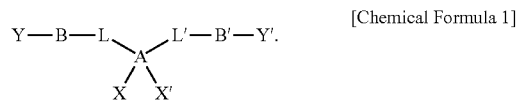

[Chemical Formula 1]

8 Claims, No Drawings

(56) References Cited

FOREIGN PATENT DOCUMENTS

| KR | 10-1067826 | * | 9/2011 |
| KR | 10-2011-0113472 A | | 10/2011 |
| KR | 10-2011-0139118 A | | 12/2011 |
| KR | 10-1156489 | * | 6/2012 |
| KR | 10-2013-0078745 A | | 7/2013 |
| PL | 192759 | * | 12/2006 |

OTHER PUBLICATIONS

Manecke et al. "Darstellumng und eigenschaften chelatbildender monomerer . . . " Makromol. Chem., vol. 133(3267) pp. 61-82 (1970).*
Janser et al., "Formation of triple stranded dinuclear helicates . . . ", Eur. J. Inorg. Chem., pp. 244-251 (2006).*
Taiwanese Search Report dated Oct. 26, 2015 in Corresponding Taiwanese Patent Application No. 104105454.
Chinese Office action dated Jul. 1, 2016 in corresponding Chinese Patent Application No. 201510043403.9.
Von Georg Manecke et al., Die Makromolekulare Chemie 133, (1970) p. 61-82.
Ingo Janser et al., Eur. J. Inorg. Chem., (2006) p. 244-251.
Ismet Kaya et al., Reztive & Functional Polymers 70, (2010) p. 815-826.

* cited by examiner

MONOMER FOR HARDMASK COMPOSITION, HARDMASK COMPOSITION INCLUDING THE MONOMER, AND METHOD OF FORMING PATTERNS USING THE HARDMASK COMPOSITION

CROSS-REFERENCE TO RELATED APPLICATION

Korean Patent Application No. 10-2014-0032392, filed on Mar. 19, 2014, in the Korean Intellectual Property Office, and entitled: "Monomer for Hardmask Composition and Hardmask Composition Including the Monomer and Method of Forming Patterns Using the Hardmask Composition," is incorporated by reference herein in its entirety.

BACKGROUND

1. Field

Embodiments relate to a monomer, a hardmask composition including the monomer, and a method of forming patterns using the hardmask composition.

2. Description of the Related Art

Recently, the semiconductor industry has developed to an ultra-fine technique having a pattern of several to several tens nanometer size. Such an ultra-fine technique uses effective lithographic techniques. One lithographic technique includes providing a material layer on a semiconductor substrate; coating a photoresist layer thereon; exposing and developing the same to provide a photoresist pattern; and etching the material layer using the photoresist pattern as a mask.

SUMMARY

Embodiments are directed to a monomer, a hardmask composition including the monomer, and a method of forming patterns using the hardmask composition.

The embodiments may be realized by providing a monomer for a hardmask composition, the monomer being represented by the following Chemical Formula 1:

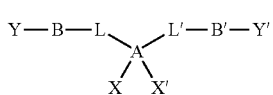

[Chemical Formula 1]

wherein, in the Chemical Formula 1, A, B, and B' are each independently a substituted or unsubstituted aliphatic cyclic moiety or a substituted or unsubstituted aromatic ring-containing moiety, L and L' are each independently —C(=O)NH—, —C(=O)O—, or —C(H)=N—, X and X' are each independently hydrogen, a halogen atom, a hydroxy group, a thionyl group, a thiol group, a cyano group, a substituted or unsubstituted amino group, a substituted or unsubstituted C1 to C20 alkylamine group, a substituted or unsubstituted C1 to C20 aldehyde group, a substituted or unsubstituted carboxyl group, or a combination thereof, and Y and Y' are each independently hydrogen, a halogen atom, a hydroxy group, a thionyl group, a thiol group, a cyano group, a substituted or unsubstituted amino group, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C30 alkoxy group, a substituted or unsubstituted C2 to C30 alkenyl group, a substituted or unsubstituted C2 to C30 alkynyl group, substituted or unsubstituted C1 to C20 aldehyde group, a substituted or unsubstituted C1 to C4 alkylether, a substituted or unsubstituted C7 to C20 arylalkylene ether, a substituted or unsubstituted C1 to C30 haloalkyl group, or a combination thereof.

A may be a substituted or unsubstituted moiety of the following Group 1:

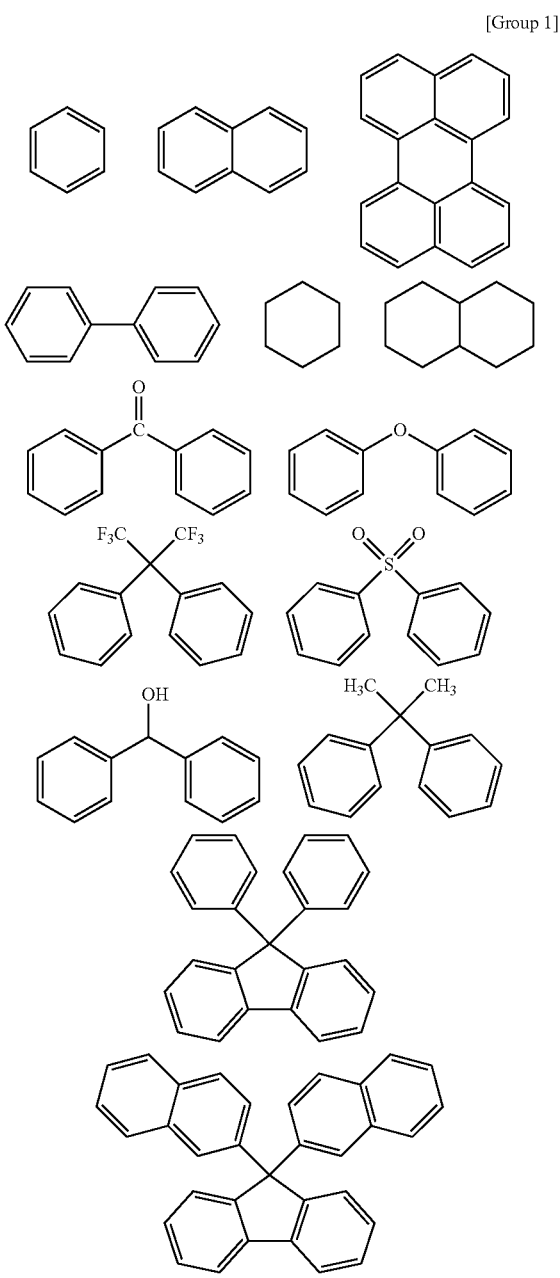

[Group 1]

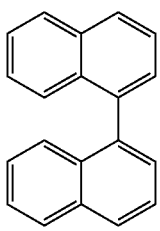
wherein X, X', L, or L' may be linked to the substituted or unsubstituted moiety of Group 1 at any ring atom of the substituted or unsubstituted cyclic moiety of Group 1.
B and B' may each independently be a substituted or unsubstituted moiety of the following Group 2:
[Group2]
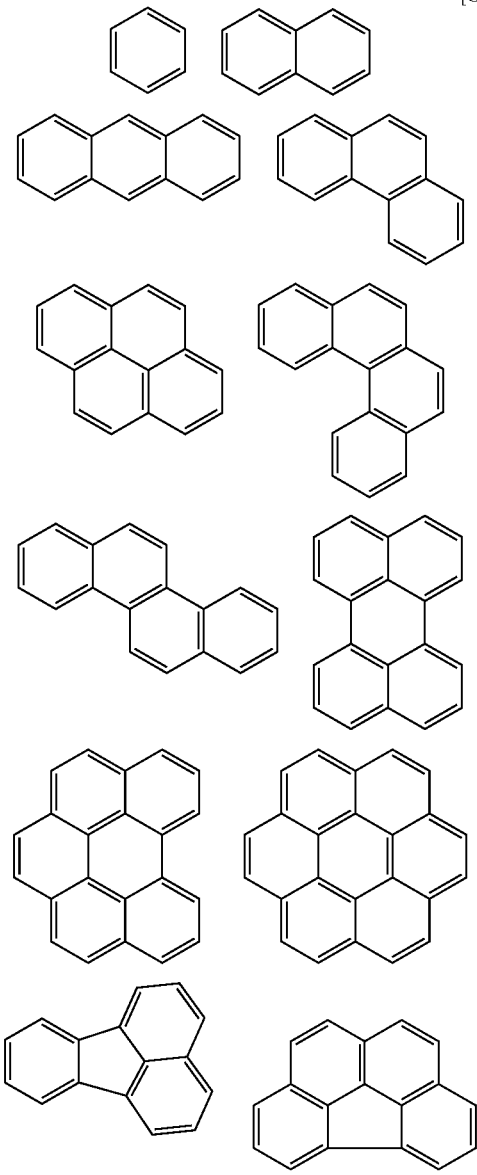
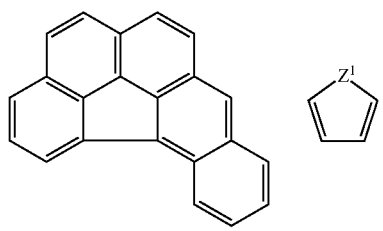
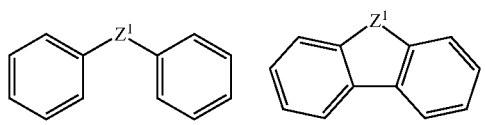
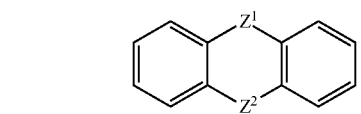
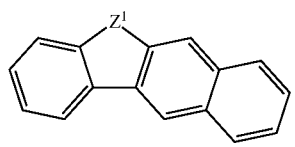
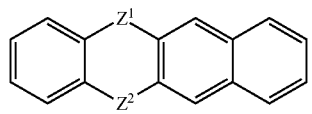
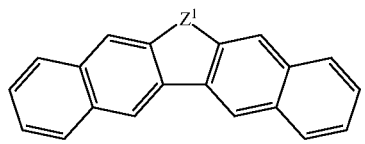
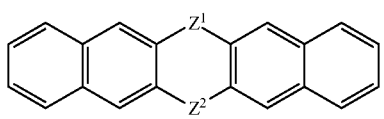
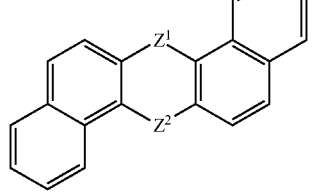
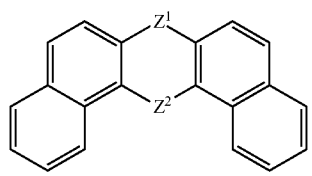

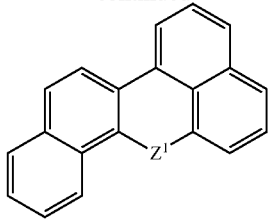

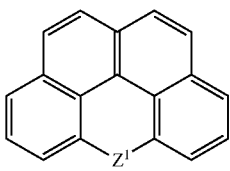

wherein, in Group 2, $Z^1$ and $Z^2$ may each independently be a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR, oxygen (O), sulfur (S), or a combination thereof, R may be hydrogen, a substituted or unsubstituted C1 to C10 alkyl group, a halogen atom, a halogen-containing group, or a combination thereof, and wherein Y, Y', L, or L' may be linked to the substituted or unsubstituted moiety of Group 2 at any ring atom of the substituted or unsubstituted cyclic moiety of Group 2.

The monomer represented by Chemical Formula 1 may be represented by one of the following Chemical Formulae 2 to 5:

[Chemical Formula 2]

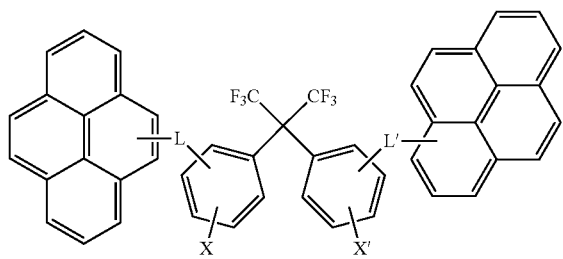

[Chemical Formula 3]

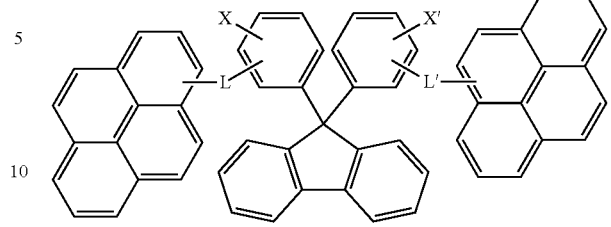

[Chemical Formula 4]

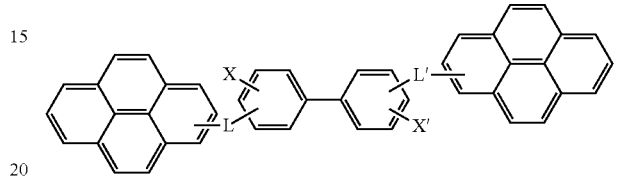

[Chemical Formula 5]

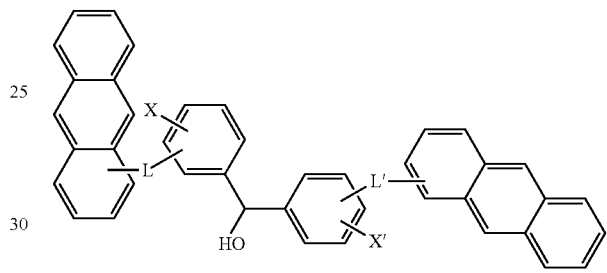

wherein, in Chemical Formulae 2 to 5, L and L' may each independently be —C(=O)NH—, —C(=O)O—, or —C(H)=N—, and X and X' may each independently be hydrogen, a halogen atom, a hydroxy group, a thionyl group, a thiol group, a cyano group, a substituted or unsubstituted amino group, a substituted or unsubstituted C1 to C20 alkylamine group, a substituted or unsubstituted C1 to C20 aldehyde group, a substituted or unsubstituted carboxyl group, or a combination thereof.

L and L' may each independently be —C(=O)NH— or —C(H)=N—, and X and X' may each independently be a hydroxy group or a substituted or unsubstituted amino group.

The monomer may have a molecular weight of about 800 to about 5,000.

The monomer represented by Chemical Formula 1 may be represented by one of the following Chemical Formulae A to D:

[Chemical Formula A]

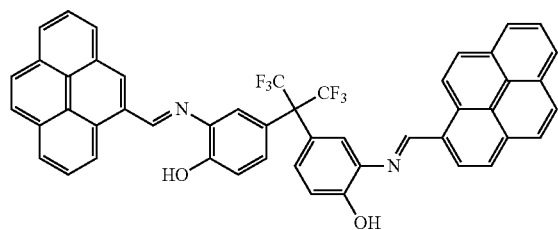

[Chemical Formula B]

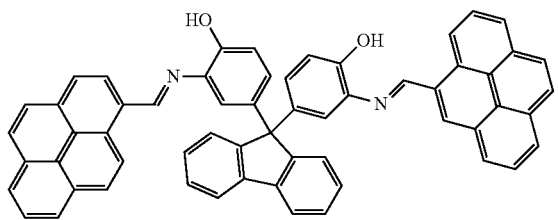

-continued

[Chemical Formula C]

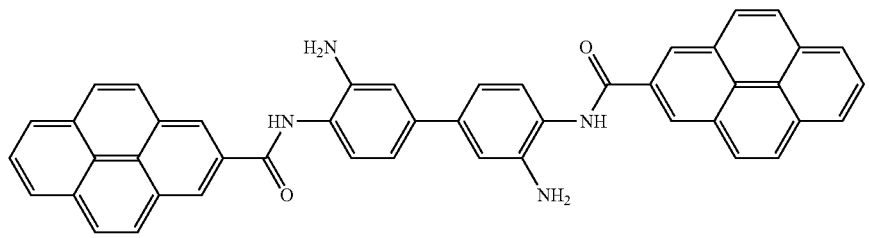

[Chemical Formula D]

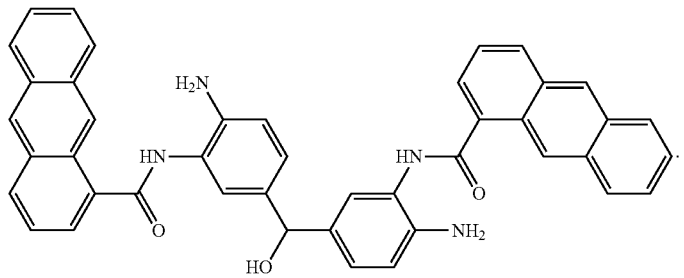

The embodiments may be realized by providing a hardmask composition including a solvent; and a monomer represented by the following Chemical Formula 1:

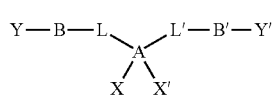

[Chemical Formula 1]

wherein, in Chemical Formula 1, A, B, and B' are each independently a substituted or unsubstituted aliphatic cyclic moiety or a substituted or unsubstituted aromatic ring-containing moiety, L and L' are each independently —C(=O)NH—, —C(=O)O—, or —C(H)=N—, X and X' are each independently hydrogen, a halogen atom, a hydroxy group, a thionyl group, a thiol group, a cyano group, a substituted or unsubstituted amino group, a substituted or unsubstituted C1 to C20 alkylamine group, a substituted or unsubstituted C1 to C20 aldehyde group, a substituted or unsubstituted carboxyl group, or a combination thereof, and Y and Y' are each independently hydrogen, a halogen atom, a hydroxy group, a thionyl group, a thiol group, a cyano group, a substituted or unsubstituted amino group, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C30 alkoxy group, a substituted or unsubstituted C2 to C30 alkenyl group, a substituted or unsubstituted C2 to C30 alkynyl group, substituted or unsubstituted C1 to C20 aldehyde group, a substituted or unsubstituted C1 to C4 alkylether, a substituted or unsubstituted C7 to C20 arylalkylene ether, a substituted or unsubstituted C1 to C30 haloalkyl group, or a combination thereof.

A may be a substituted or unsubstituted moiety of the following Group 1:

[Group 1]

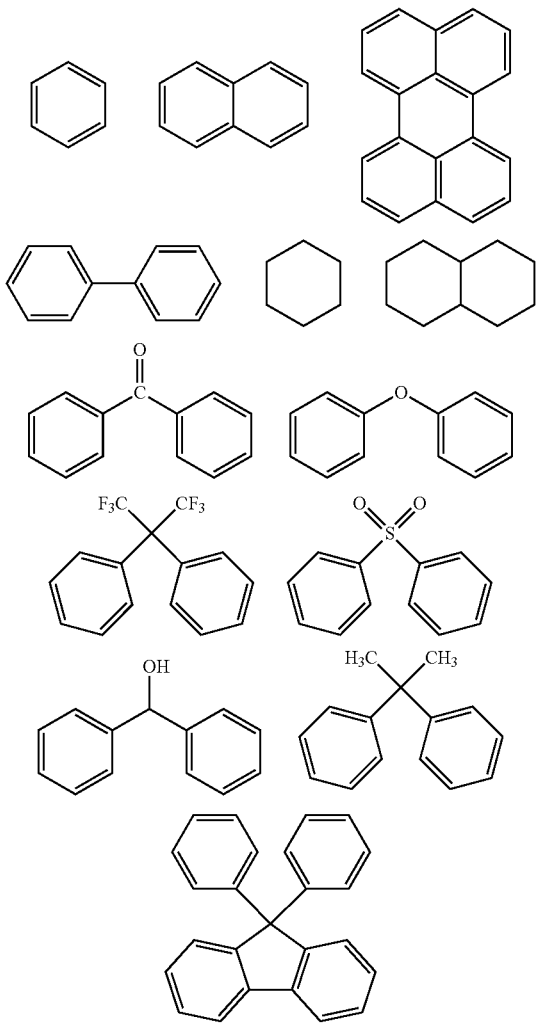

-continued
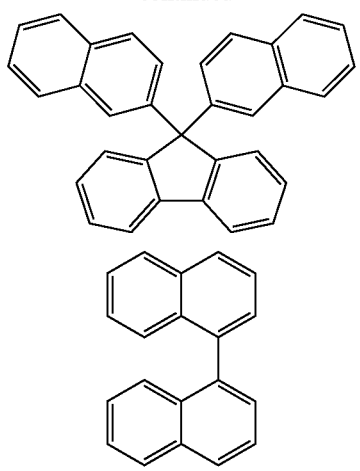
wherein X, X', L, or L' may be linked to the substituted or unsubstituted moiety of Group 1 at any ring atom of the substituted or unsubstituted moiety of Group 1.
B and B' may each independently be a substituted or unsubstituted moiety of the following Group 2:
[Group 2]
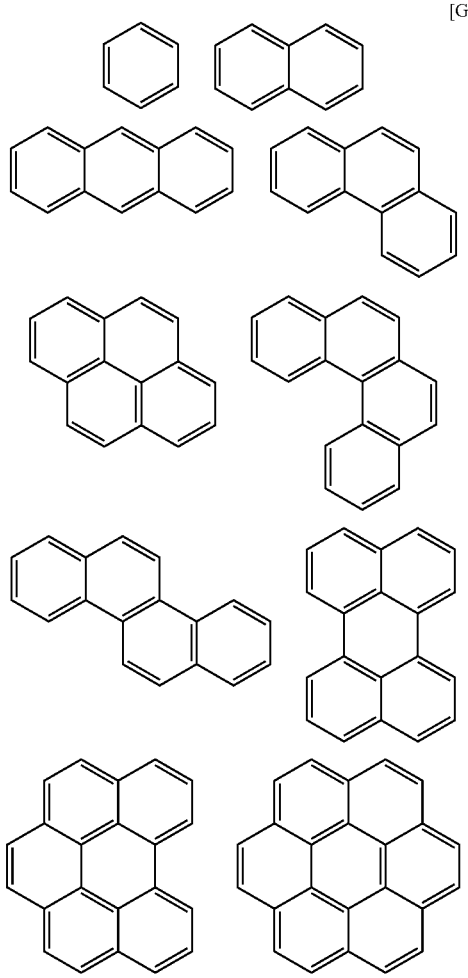
-continued
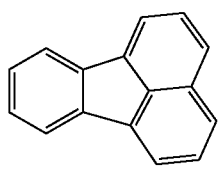
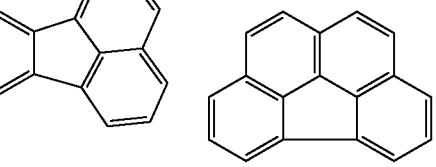
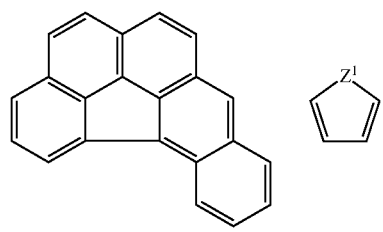
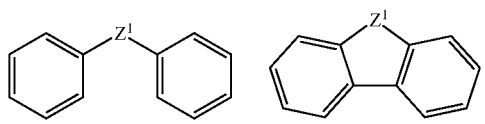
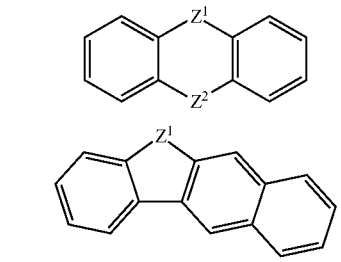
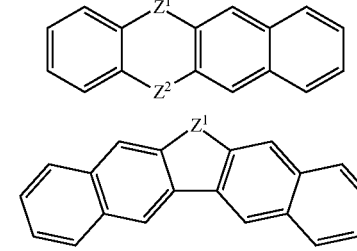
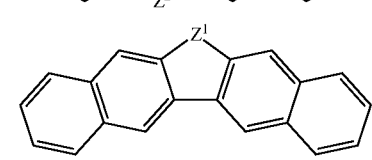
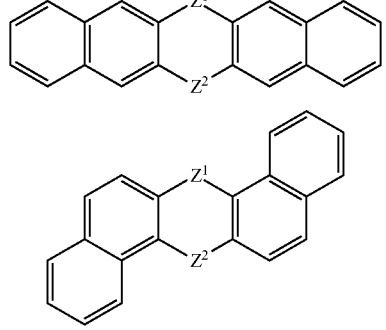
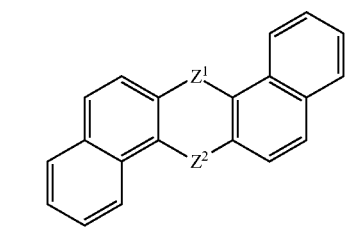
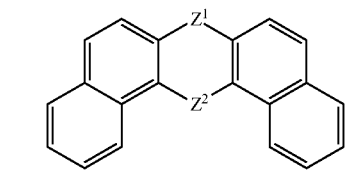

-continued

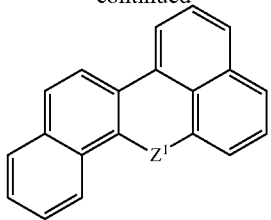

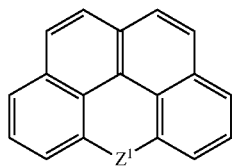

wherein, in Group 2, $Z^1$ and $Z^2$ may each independently be a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR, oxygen (O), sulfur (S), or a combination thereof, R may be hydrogen, a substituted or unsubstituted C1 to C10 alkyl group, a halogen atom, a halogen-containing group, or a combination thereof, and wherein Y, Y', L, or L' may be linked to the substituted or unsubstituted moiety of Group 2 at any ring atom of the substituted or unsubstituted moiety of Group 2.

The monomer represented by Chemical Formula 1 may be represented by one of the following Chemical Formulae 2 to 5:

[Chemical Formula 2]

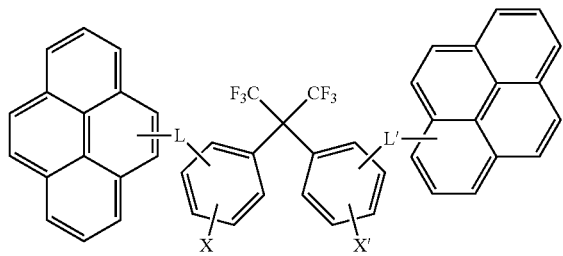

[Chemical Formula 3]

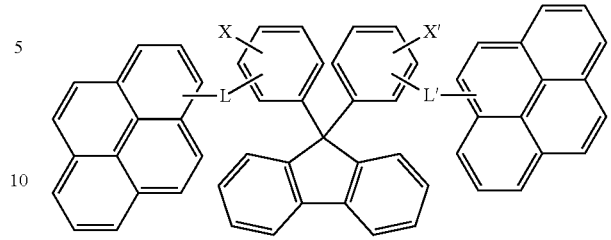

[Chemical Formula 4]

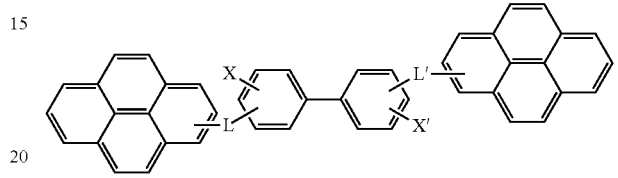

[Chemical Formula 5]

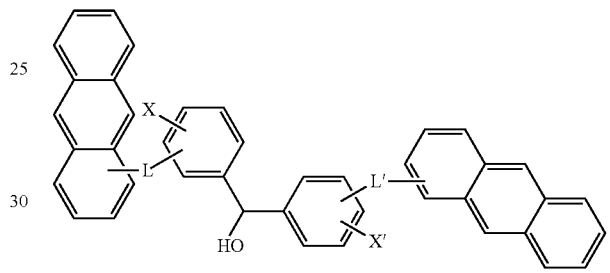

wherein, in Chemical Formulae 2 to 5, L and L' may each independently be —C(=O)NH—, —C(=O)O—, or —C(H)=N—, and X and X' may each independently be hydrogen, a halogen atom, a hydroxy group, a thionyl group, a thiol group, a cyano group, a substituted or unsubstituted amino group, a substituted or unsubstituted C1 to C20 alkylamine group, a substituted or unsubstituted C1 to C20 aldehyde group, a substituted or unsubstituted carboxyl group, or a combination thereof.

L and L' may each independently be —C(=O)NH— or —C(H)=N—, and X and X' may each independently be a hydroxy group or a substituted or unsubstituted amino group.

When the hardmask composition is heat-treated at about 100 to about 500° C. for about 60 seconds to about 20 minutes, the monomer may form a structure represented by one of the following Chemical Formulae 6 to 9:

[Chemical Formula 6]

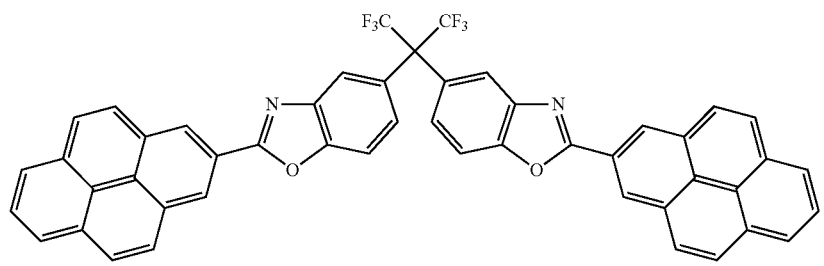

-continued

[Chemical Formula 7]

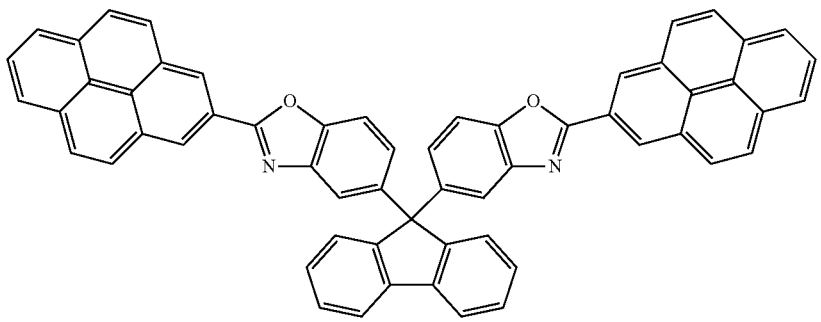

[Chemical Formula 8]

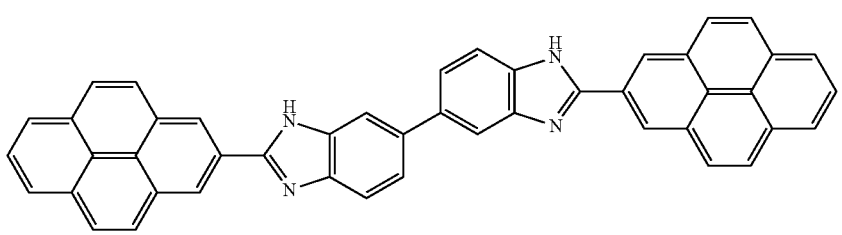

[Chemical Formula 9]

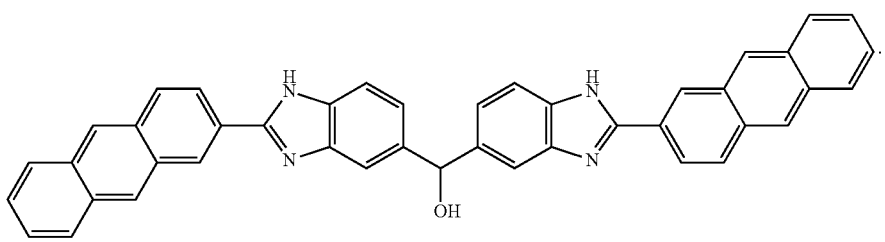

The monomer may have a molecular weight of about 800 to about 5,000.

The monomer may be included in the composition in an amount of about 0.1 wt % to about 30 wt %, based on a total weight of the hardmask composition.

The embodiments may be realized by providing a method of forming patterns, the method including providing a material layer on a substrate, applying the hardmask composition according to an embodiment on the material layer, heat-treating the hardmask composition to form a hardmask layer, forming a silicon-containing thin layer on the hardmask layer, forming a photoresist layer on the silicon-containing thin layer, exposing and developing the photoresist layer to form a photoresist pattern; selectively removing the silicon-containing thin layer and the hardmask layer using the photoresist pattern to expose a part of the material layer, and etching an exposed part of the material layer.

Applying the hardmask composition may include spin-on coating.

Heat-treating the hardmask composition to form the hardmask layer may include heat-treating at about 100° C. to about 500° C.

The method may further include forming a bottom anti-reflective coating on the silicon-containing thin layer.

The silicon-containing thin layer may include silicon oxynitride.

DETAILED DESCRIPTION

Example embodiments will now be described more fully hereinafter; however, they may be embodied in different forms and should not be construed as limited to the embodiments set forth herein. Rather, these embodiments are provided so that this disclosure will be thorough and complete, and will fully convey exemplary implementations to those skilled in the art.

As used herein, when a definition is not otherwise provided, the term 'substituted' may refer to one substituted with a substituent selected from a halogen atom (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C2 to C20 alkenyl group, a C2 to C20 alkynyl group, a C6 to C30 aryl group, a C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C30 heterocycloalkyl group, and a combination thereof, instead of a hydrogen atom of a compound.

As used herein, when a definition is not otherwise provided, the term 'hetero' refers to one including 1 to 3 heteroatoms selected from B, N, O, S, and P.

Hereinafter, a monomer for a hardmask composition according to one embodiment is described.

The monomer for a hardmask composition according to an embodiment may be represented by the following Chemical Formula 1.

[Chemical Formula 1]

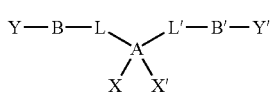

In Chemical Formula 1,

A, B, and B' may each independently be or include a substituted or unsubstituted aliphatic cyclic group or moiety or a substituted or unsubstituted aromatic ring-containing group or moiety, L and L' may each independently be —C(=O)NH—, —C(=O)O—, or —C(H)=N—, X and X' may each independently be hydrogen, a halogen atom, a hydroxy group, a thionyl group, a thiol group, a cyano group, a substituted or unsubstituted amino group, a substituted or unsubstituted C1 to C20 alkylamine group, a substituted or unsubstituted C1 to C20 aldehyde group, a substituted or unsubstituted carboxyl group, or a combination thereof, and Y and Y' may each independently be hydrogen, a halogen atom, a hydroxy group, a thionyl group, a thiol group, a cyano group, a substituted or unsubstituted amino group, a substituted or unsubstituted C1 to C30 alkyl group, a substituted or unsubstituted C3 to C30 cycloalkyl group, a substituted or unsubstituted C6 to C30 aryl group, a substituted or unsubstituted C3 to C30 cycloalkenyl group, a substituted or unsubstituted C1 to C20 alkylamine group, a substituted or unsubstituted C7 to C20 arylalkyl group, a substituted or unsubstituted C1 to C20 heteroalkyl group, a substituted or unsubstituted C2 to C30 heterocycloalkyl group, a substituted or unsubstituted C2 to C30 heteroaryl group, a substituted or unsubstituted C1 to C30 alkoxy group, a substituted or unsubstituted C2 to C30 alkenyl group, a substituted or unsubstituted C2 to C30 alkynyl group, substituted or unsubstituted C1 to C20 aldehyde group, a substituted or unsubstituted C1 to C4 alkylether, a substituted or unsubstituted C7 to C20 arylalkylene ether, a substituted or unsubstituted C1 to C30 haloalkyl group, or a combination thereof. In an implementation, the monomer may include at least one functional group that forms a ring by combination with L or L'.

In an implementation, the monomer may have a structure including an aromatic ring-containing group or moiety (having one or more than one ring) as a core and a substituent including an aromatic ring-containing group or moiety at sides, e.g., both sides, of the core. The core and the substituent may include a plurality of functional groups (e.g., X, X', Y, and Y'). The functional groups may help further improve solubility of or in the hardmask composition. Thus, the composition may not only be effectively spin-on coated but may also bring about excellent gap-fill characteristics and planarization characteristics of filling gaps among patterns when the hardmask composition is spin-on coated on a lower layer having a predetermined pattern.

In addition, the plurality of functional groups may be capable of amplification-cross-linking through a condensation reaction and may help realize excellent cross-linking characteristics. Accordingly, the monomer may be cross-linked into a polymer having a high molecular weight, even when a heat treatment is performed on the composition at a relatively low temperature for a relatively short time, and may realize characteristics suitable for a hardmask layer (e.g., excellent mechanical characteristics, heat resistance properties, and etch resistance).

The aromatic ring-containing groups of the core and the substituent may be connected by a linking group of, e.g., —C(=O)NH—, —C(=O)O—, or —C(H)=N—. The linking group may react with a functional group (X and X') and may form a ring, e.g., a fused ring, in or with the core when the hardmask composition is heat-treated. Thus, the monomer may help remarkably improve etch resistance and heat resistance. For example, the monomer may be a benzoxazole precursor or an imidazole precursor.

For example, A of Chemical Formula 1 may be or may include a substituted or unsubstituted cyclic moiety. For example, the cyclic moiety may be illustrated in the following Group 1.

[Group 1]

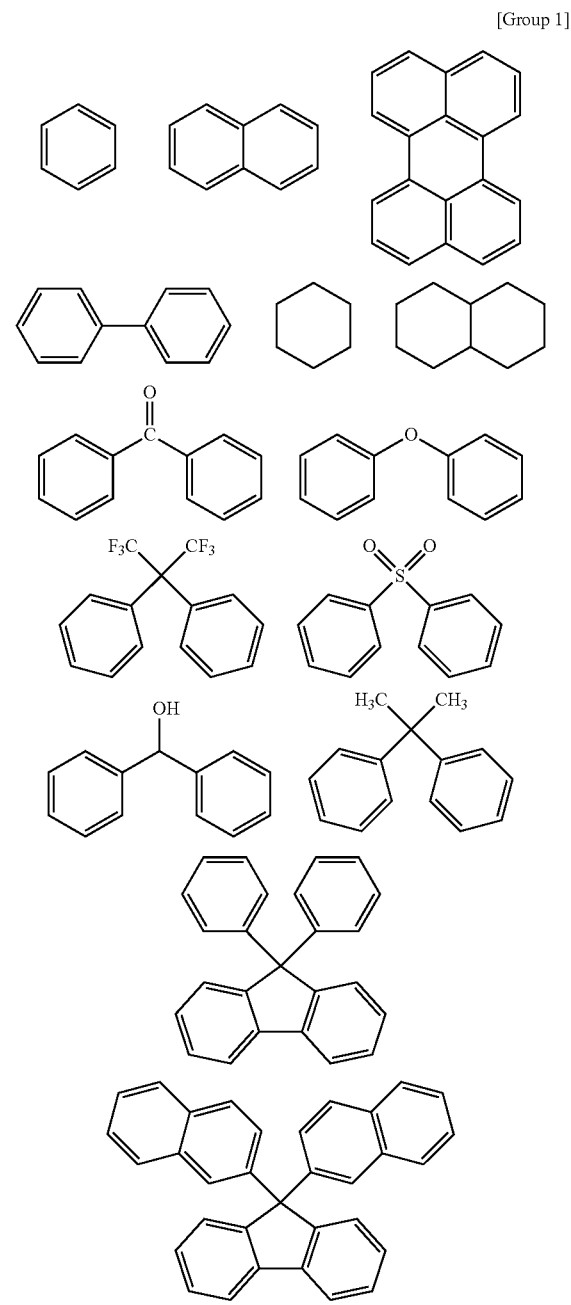

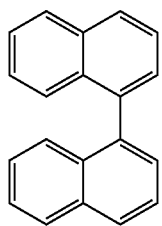
For example, the B and B' may be or may include a substituted or unsubstituted cyclic moiety. For example, the cyclic moiety may be illustrated in the following Group 2.
[Group 2]
 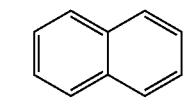
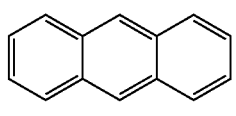 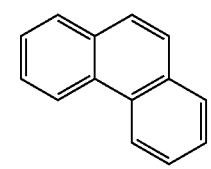
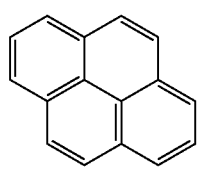 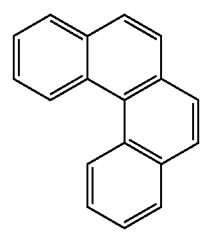
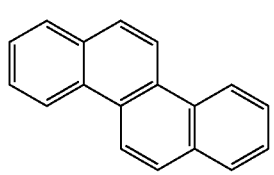 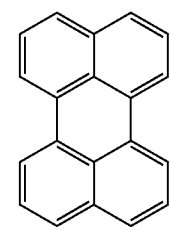
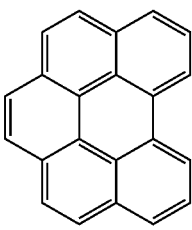 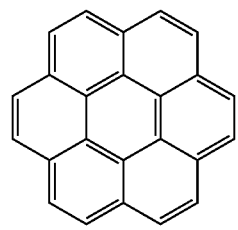
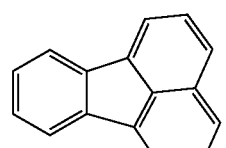 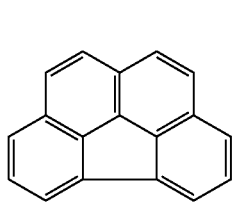
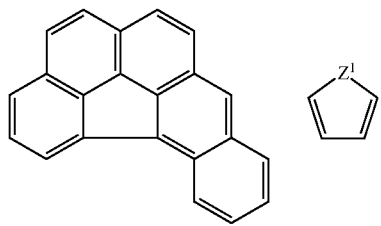
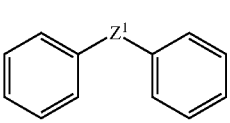 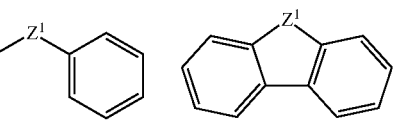
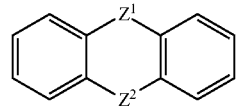
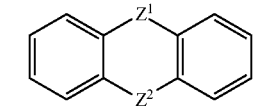
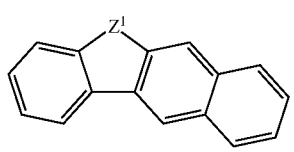
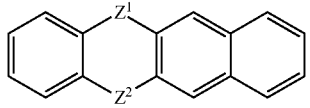
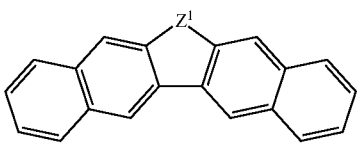
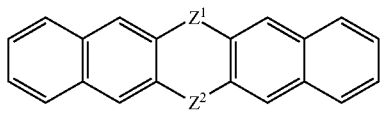
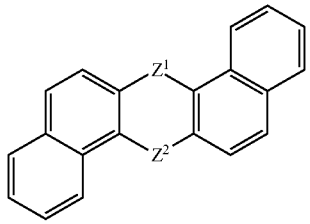
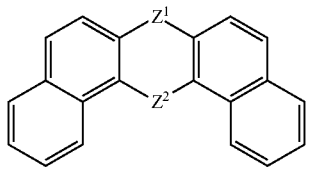

-continued

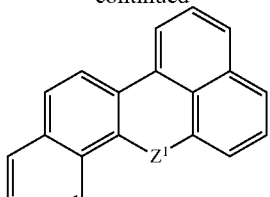

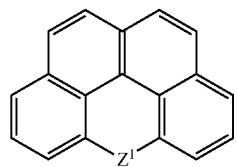

In Group 2, $Z^1$ and $Z^2$ may each independently be a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR, oxygen (O), sulfur (S), or a combination thereof, and R may be hydrogen, a substituted or unsubstituted C1 to C10 alkyl group, a halogen atom, a halogen-containing group, or a combination thereof.

In Groups 1 and 2, a linking position of each ring, e.g., to other groups or moieties (e.g., X, X', L, L', Y, and/or Y') of the compound of Chemical Formula 1, is not particularly limited. For example, the moieties of Groups 1 and/or 2 may be linked at suitable or available linking positions thereof to thus be included as a moiety of the compound represented by Chemical Formula 1.

In an implementation, the monomer may be represented by one of the following Chemical Formulae 2 to 5.

[Chemical Formula 2]

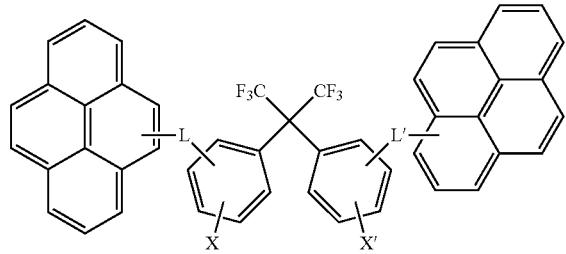

[Chemical Formula 3]

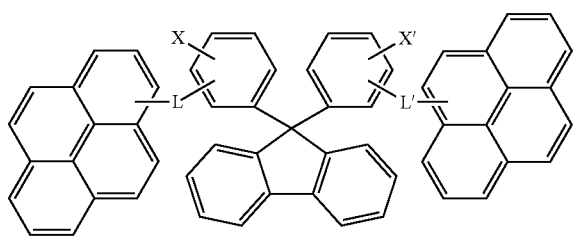

[Chemical Formula 4]

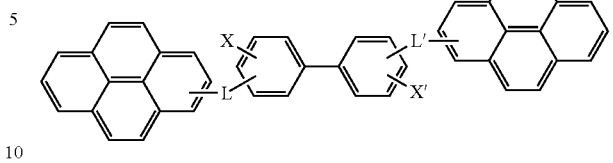

[Chemical Formula 5]

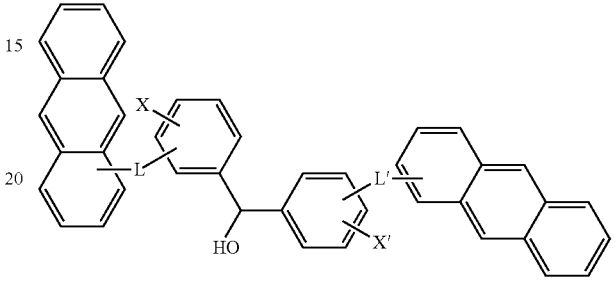

In Chemical Formulae 2 to 5,

L and L' may each independently be —C(=O)NH—, —C(=O)O—, or —C(H)=N—, and

X and X' may each independently be hydrogen, a halogen atom, a hydroxy group, a thionyl group, a thiol group, a cyano group, a substituted or unsubstituted amino group, a substituted or unsubstituted C1 to C20 alkylamine group, a substituted or unsubstituted C1 to C20 aldehyde group, a substituted or unsubstituted carboxyl group, or a combination thereof.

In an implementation, L and L' of the monomer represented by the Chemical Formula 1 may each independently be, e.g., —C(=O)NH— or —C(H)=N—, and X and X' may each independently be, e.g., a hydroxy group or a substituted or unsubstituted amino group.

The monomer may have a molecular weight of about 800 to about 5,000. When the monomer has a molecular weight within the above range, solubility of the monomer (having high carbon content) in a solvent may be improved, and an improved thin layer may be obtained through spin-on coating.

Hereinafter, a hardmask composition according to one embodiment is described.

A hardmask composition according to one embodiment may include the monomer and a solvent.

The monomer may be the same as described above. In an implementation, in the composition, one kind of monomer may be used singularly, or two or more kinds of monomers may be mixed.

When the hardmask composition is heat-treated, the monomer may be cyclized through interaction between the linking group (e.g., L and/or L') of —C(=O)NH—, —C(=O)O—, or —C(H)=N— and other functional groups (e.g., X and/or X'). As a result, the monomer in the heat-treated hardmask composition may include, e.g., a benzoxazole or imidazole structure represented by one of the following Chemical Formulae 6 to 9.

[Chemical Formula 6]

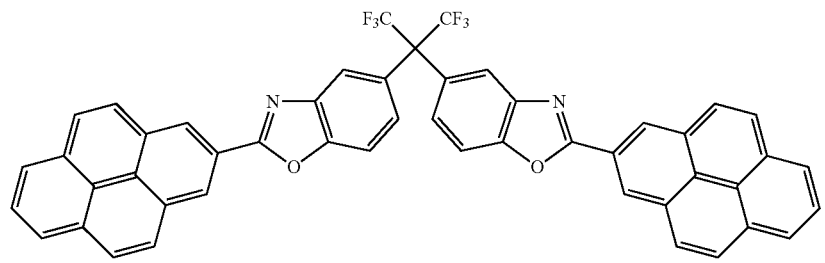

[Chemical Formula 7]

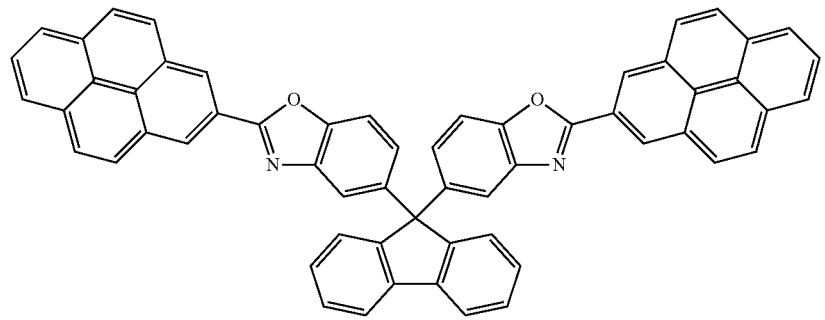

[Chemical Formula 8]

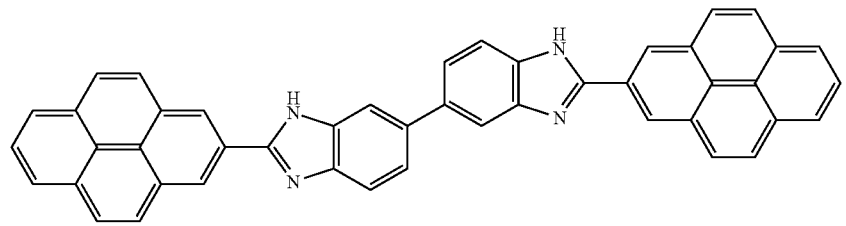

[Chemical Formula 9]

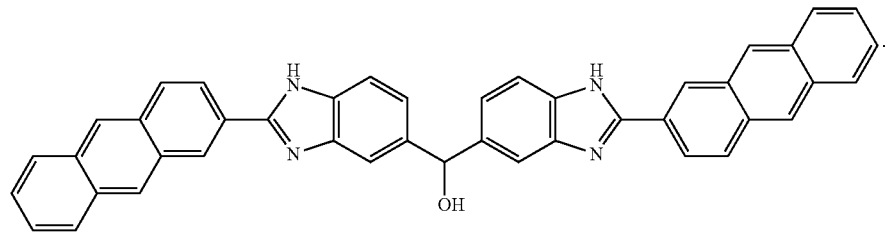

The cyclization reaction may occur, e.g., through a baking or heat treating process at about 100 to about 500° C. for about 60 seconds to about 20 minutes. The baking process may include a heat treatment after coating the hardmask composition on a substrate.

The solvent may have sufficient solubility or dispersion with respect to the monomer. In an implementation, the solvent may include, e.g., propylene glycol, propylene glycol diacetate, methoxy propanediol, diethylene glycol, diethylene glycol butylether, tri(ethylene glycol)monomethylether, propylene glycol monomethylether, propylene glycol monomethylether acetate, cyclohexanone, ethyllactate, gamma-butyrolactone, methylpyrrolidone, acetylacetone, or ethyl 3-ethoxypropionate.

The monomer may be included in the composition in an amount of, e.g., about 0.1 to about 30 wt %, based on a total weight of the hardmask composition. When the monomer is included in the above range, a desired thickness of a coated thin film may be obtained.

In an implementation, the hardmask composition may further include a surfactant.

The surfactant may include, e.g., alkylbenzene sulfonate salt, alkyl pyridinium salt, polyethylene glycol, or a quaternary ammonium salt.

The surfactant may be included in the composition in an amount of, e.g., about 0.001 to about 3 parts by weight, based on 100 parts by weight of the hardmask composition. Within the range, solubility may be secured while not changing the optical properties of the hardmask composition.

Hereafter, a method for forming patterns by using the hardmask composition is described.

A method of forming patterns according to one embodiment may include, e.g., providing a material layer on a substrate, applying the hardmask composition (including the monomer and solvent) on the material layer, heat-treating the hardmask composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

The substrate may be, e.g., a silicon wafer, a glass substrate, or a polymer substrate.

The material layer may be a material to be finally patterned, e.g., a metal layer such as an aluminum layer or a copper layer, a semiconductor layer such as a silicon layer, or an insulation layer such as a silicon oxide layer or a silicon nitride layer. The material layer may be formed through a method such as a chemical vapor deposition (CVD) process.

The hardmask composition may be applied by, e.g., spin-on coating in a form of a solution. In an implementation, a thickness of the hardmask composition may be, e.g., about 100 Å to about 10,000 Å.

Heat-treating the hardmask composition may be performed, e.g., about 100 to about 500° C. for about 60 seconds to 20 minutes. During heat-treating, the monomer may undergo a self cross-linking and/or a mutual cross-linking reaction.

The silicon-containing thin layer may be made of, e.g., silicon nitride, silicon oxide, or silicon oxynitride (SiON).

In an implementation, the method may further include forming a bottom antireflective coating (BARC) on the silicon-containing thin layer before forming the photoresist layer.

Exposure of the photoresist layer may be performed using, e.g., ArF, KrF, or EUV. After exposure, a heat treatment may be performed at about 100° C. to about 500° C.

The etching process of the exposed part of the material layer may be performed through a dry etching process using an etching gas and the etching gas may be, e.g., $CHF_3$, $CF_4$, $Cl_2$, $BCl_3$, or a mixed gas thereof.

The etched material layer may be formed in a plurality of patterns, and the plurality of patterns may include a metal pattern, a semiconductor pattern, an insulation pattern, or the like, e.g., diverse patterns of a semiconductor integrated circuit device.

Hereinafter, the present disclosure is illustrated in more detail with reference to examples. However, these examples are exemplary, and the present disclosure is not limited thereto.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHESIS OF MONOMER

Synthesis Example 1

2.39 g of 2,2-bis(3-amino-4-hydroxyphenyl)-hexafluoropropane, 3.00 g of pyrenecarboxaldehyde, and 15 ml of ethanol were put in a 50 ml flask and refluxed at 90° C. When the pyrenecarboxaldehyde disappeared on thin film chromatography (TLC), the reactor was cooled down to ambient temperature, and a solid produced therein was filtered and cleaned with 50 ml of ethanol, obtaining 4.05 g of a compound (monomer) represented by the following Chemical Formula A.

[Chemical Formula A]

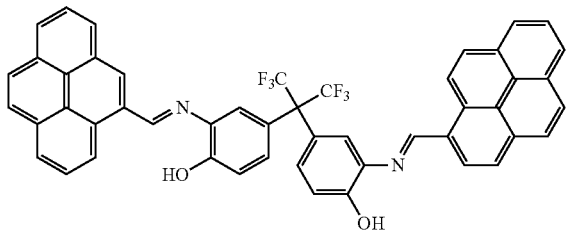

Synthesis Example 2

2.48 g of 9,9-bis(3-amino-4-hydroxyphenyl)fluorene, 3.00 g of pyrenecarboxaldehyde and 28 ml of ethanol were put in a 100 ml flask and then, refluxed at 90° C. When the pyrenecarboxaldehyde disappeared on thin film chromatography (TLC), the reactor was cooled town to ambient temperature, and a solid produced therein was filtered and cleaned with 20 ml of ethanol, obtaining 4.05 g of a compound (monomer) represented by the following Chemical Formula B.

[Chemical Formula B]

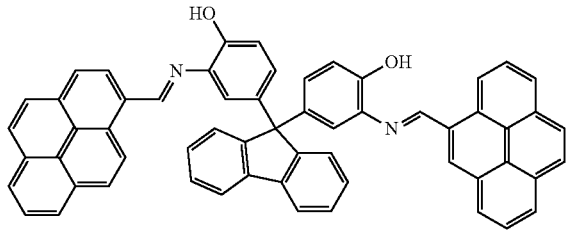

Synthesis Example 3

1.30 g of 1,3'-diaminobenzidine, 3.00 g of 1-pyrenecarboxylic acid and 30 ml of tetrahydrofuran (THF) were put in a 100 mL flask and agitated with a stirring magnet at ambient temperature for 20 hours. Subsequently, a precipitate obtained from the mixed solution was filtered to obtain a powder, and the powder was rinsed several times with n-hexane, obtaining 3.8 g of a compound (monomer) represented by the following Chemical Formula C.

[Chemical Formula C]

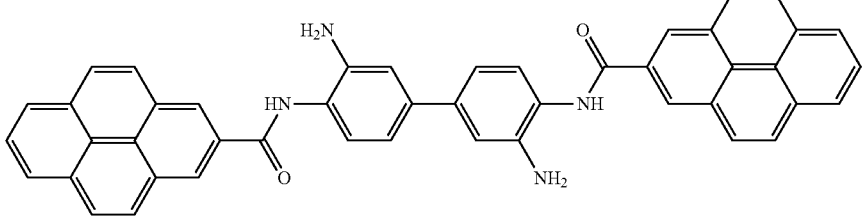

Synthesis Example 4

3 g of 1-anthracenecarboxylic acid, 1.65 g of bis(3,4-diaminophenyl)methanol and tetrahydrofuran (THF) were put in a 50 mL flask and agitated with a stirring magnet at ambient temperature for 20 hours. Subsequently, a precipitate produced in the mixed solution was filtered and rinsed several times with n-hexane, obtaining 3.52 g of a compound (monomer) represented by the following Chemical Formula D.

[Chemical Formula D]

Comparative Synthesis Example 1

First Step: Friedel-Crafts Acylation Reaction 50.0 g (0.166 mol) of coronene, 46.8 g (0.333 mol) of benzoylchloride, and 330 g of 1,2-dichloroethane were put in a flask, preparing a solution. Subsequently, 44.4 g (0.333 mol) of aluminum chloride was slowly added to the solution at ambient temperature, and the mixture was heated up to 60° C. for 8 hours. When the reaction was complete, methanol was added to the solution, and a precipitate produced therein was filtered and dried.

Second Step: Demethylation Reaction 25.0 g (0.0492 mol) of the compound (from the first step) and 174 g of tetrahydrofuran were put in a flask, preparing a solution. Subsequently, 18.6 g (0.492 mol) of a sodium borohydride aqueous solution was slowly added to the solution, and the mixture was agitated at ambient temperature for 24 hours. When the reaction was complete, the resultant was neutralized with a 5% hydrogen chloride solution to pH 7 and then, extracted with ethyl acetate and dried, obtaining a compound represented by the following Chemical Formula E.

[Chemical Formula E]

Comparative Synthesis Example 2

10 g (0.057 mol) of benzylmethacrylate and 10.6 g (0.057 mol) of cyclohexylmethylmethacrylate were mixed with 41 g of methylethylketone in a flask under a nitrogen atmosphere. Then, 2.6 g of dimethyl-2,2'-azobis(2-methylpropionate) as a polymerization initiator was added to the mixture at 80° C. for 4 hours with a syringe for 2 hours. When the polymerization was complete, the obtained polymer was slowly precipitated in an excess of a hexane solvent. Then, a precipitate produced therein was filtered and dissolved in an appropriate amount of a hexane/isopropanol mixed solvent, and then, the solution was agitated. Subsequently, the obtained precipitate was dried in a 50° C. vacuum oven for about 24 hours, obtaining a compound represented by Chemical Formula F.

The obtained polymer had a weight average molecular weight (Mw) of 6,200 and polydispersity (Mw/Mn) of 1.45.

[Chemical Formula F]

(a:b = 1:1)

Preparation of Hardmask Composition

Example 1

The compound according to Synthesis Example 1 was dissolved in a mixed solvent (obtained by mixing propylene glycol monomethyl ether acetate (PGMEA) and cyclohexanone (7:3 (v/v))), and the solution was filtered, preparing a hardmask composition. The amount of the compound was adjusted in an amount of 10.0 wt % or 13.0 wt %, based on the total weight of the hardmask composition (with a view toward a desired thickness).

Example 2

A hardmask composition was prepared according to the same method as Example 1, except for using the compound of Synthesis Example 2 instead of the compound according to Synthesis Example 1.

Example 3

A hardmask composition was prepared according to the same method as Example 1, except for using the compound of Synthesis Example 3 instead of the compound according to Synthesis Example 1.

Example 4

A hardmask composition was prepared according to the same method as Example 1, except for using the compound of Synthesis Example 4 instead of the compound according to Synthesis Example 1.

Comparative Example 1

A hardmask composition was prepared according to the same method as Example 1, except for using the compound of Comparative Synthesis Example 1 instead of the compound according to Synthesis Example 1.

Comparative Example 2

A hardmask composition was prepared according to the same method as Example 1, except for using the compound of Comparative Synthesis Example 2 instead of the compound according to Synthesis Example 1.

Evaluation

Evaluation 1: Heat Resistance Evaluation-1

Each hardmask composition according to Examples 1 to 4 and Comparative Examples 1 and 2 was respectively spin-on coated on a silicon wafer and heat-treated on a hot plate at 400° C. for 2 minutes, forming a thin film. The thin film was scraped and made into a pellet, a decrease in weight of the pellet after 30 minutes at 400° C. was determined, and a weight maintenance ratio was calculated (Thermogravimetric Analysis, TGA).

The results are provided in the following Table 1.

TABLE 1

| | Weight maintenance ratio (%) |
|---|---|
| Example 1 | 95.8% |
| Example 2 | 97.5% |
| Example 3 | 96.1% |
| Example 4 | 96.5% |
| Comparative Example 1 | 66.7% |
| Comparative Example 2 | 52.6% |

Referring to Table 1, each thin film formed of the hardmask compositions according to Examples 1 to 4 showed a low weight loss rate (e.g., a high weight maintenance ratio), compared with the thin films according to Comparative Examples 1 and 2. Accordingly, the hardmask compositions according to Examples 1 to 4 showed excellent heat resistance, compared with the hardmask compositions according to Comparative Examples 1 and 2.

Evaluation 2: Heat Resistance Evaluation-2

Each hardmask composition according to Examples 1 to 4 and Comparative Example 1 was spin-coated on a silicon wafer and heat-treated on a hot plate at 240° C. for 2 minute, forming a thin film. Then, the thickness of the thin film was measured. Subsequently, the thin film was further heat-treated at 400° C. for 2 minutes, and the thickness of the thin film was measured again and used to calculate a thickness decrease ratio of the thin film.

The results are provided in the following Table 2.

TABLE 2

| | Thin film thickness after heat treatment at 240° C. (Å) | Thin film thickness after heat treatment at 400° C. (Å) | Thin film thickness decrease ratio (%) |
|---|---|---|---|
| Example 1 | 3,002 | 2,625 | 12.53 |
| Example 2 | 3,214 | 3,014 | 6.22 |
| Example 3 | 2,940 | 2,647 | 9.94 |
| Example 4 | 3,022 | 2,758 | 8.71 |
| Comparative Example 1 | 2,994 | 1,973 | 34.08 |

Referring to Table 2, each thin film formed of the hardmask composition according to Examples 1 to 4 showed a low thickness decrease ratio, compared with a thin film formed of the hardmask composition according to Comparative Example 1. Accordingly, the hardmask compositions according to Examples 1 to 4 showed excellent heat resistance, compared with the hardmask composition according to Comparative Example.

Evaluation 3: Etch Resistance

Each hardmask composition according to Examples 1 to 4 and Comparative Example 2 was spin-on coated on a silicon wafer and heat-treated on a hot plate at 400° C. for 2 minutes, respectively forming a thin film. Subsequently, a thin film thickness measurement device made by K-MAC was used to measure thicknesses of the thin films. Then, the thin films were dry-etched by using mixed gas of $N_2/O_2$ and $CF_x$ gas for 60 seconds and for 100 seconds respectively, and its weight was measured again. The thicknesses of the thin film before and after the dry etching and its etching time were used to calculate a bulk etch rate (BER) according to the following Calculation Equation 1.

(Initial thin film thickness−thin film thickness after etching)/etching time (Å/s)　　[Calculation Equation 1]

The results are provided in Table 3.

TABLE 3

| | Etch rate ($N_2/O_2$, Å/s) | Etch rate ($CF_x$, Å/s) |
|---|---|---|
| Example 1 | 25.2 | 26.3 |
| Example 2 | 23.5 | 22.7 |
| Example 3 | 24.3 | 27.6 |
| Example 4 | 22.4 | 23.3 |
| Comparative Example 2 | 29.7 | 32.4 |

Referring to Table 3, each thin film formed of the hardmask compositions according to Examples 1 to 4 showed a low etch rate, due to sufficient etch resistance against etching gas, compared with the film formed of the hardmask composition according to Comparative Example 2.

Evaluation 4: Pattern Formation

A 3,000 Å-thick silicon oxide ($SiO_2$) layer was formed on a silicon wafer using a chemical vapor deposition (CVD) method. Subsequently, the hardmask compositions according to Examples 1 to 4 and Comparative Examples 1 and 2 were respectively spin-on coated on the silicon oxide layer and heat-treated on a hot plate at 240° C. for 1 minute, forming a hardmask layer.

Subsequently, a silicon nitride (SiN) layer was formed on the hardmask layer using a chemical vapor deposition (CVD) method. Subsequently, a photoresist for KrF was coated on the silicon nitride layer and heat-treated at 110° C. for 60 seconds, exposed to light by using ASML (XT: 1400, NA 0.93) exposure equipment and developed with a 2.38 wt % tetramethylammonium hydroxide (TMAH) aqueous solution.

Subsequently, the patterned photoresist was used as a mask to dry-etch the silicon nitride layer with a $CHF_3/CF_4$ mixed gas. Subsequently, the patterned silicon nitride layer was used as a mask to dry-etch the hardmask layers (formed of the hardmask compositions according to Examples 1 to 4 and Comparative Examples 1 and 2) by using $N_2/O_2$ mixed gas, and then, the patterned hardmask layers were respectively used as a mask to dry-etch the silicon oxide layers.

Then, cross-sections of the patterns of the hardmask layers and silicon oxide layers were examined by using a scanning electronic microscope (SEM).

The results are provided in Table 4.

TABLE 4

|  | Cross-section profile of hardmask layer pattern | Cross-section profile of silicon oxide layer pattern |
| --- | --- | --- |
| Example 1 | Vertical shape | Vertical shape |
| Example 2 | Vertical shape | Vertical shape |
| Example 3 | Vertical shape | Vertical shape |
| Example 4 | Vertical shape | Vertical shape |
| Comparative Example 1 | Tapered Shape | Tapered Shape |
| Comparative Example 2 | Tapered Shape | Tapered Shape |

Referring to Table 4, the hardmask layers formed of the hardmask compositions according to Examples 1 to 4 and the silicon oxide layers beneath them were all vertically patterned. The hardmask layers formed of the hardmask compositions according to Comparative Examples 1 and 2 and the silicon oxide layers beneath them were tapered up toward the upper end.

Accordingly, the hardmask compositions according to Examples 1 to 4 had excellent etching resistance and formed a satisfactory pattern, compared with the hardmask compositions according to Comparative Examples 1 and 2. Thus, a material layer beneath the hardmask layer turned out to have a satisfactory pattern.

By way of summation and review, according to small-sizing the pattern to be formed, it may be difficult to provide a fine pattern having an excellent profile using lithographic techniques. Accordingly, a layer, called a hardmask layer, may be formed between the material layer and the photoresist layer to provide a fine pattern. The hardmask layer may play a role of an intermediate layer for transferring the fine pattern of photoresist to the material layer through the selective etching process. The hardmask layer may have particular characteristics, e.g., etch resistance and the like, to be tolerated during the multiple etching processes.

An embodiment may provide a monomer for a hardmask composition that has improved heat resistance and etch resistance.

The hardmask composition may ensure gap-fill characteristics and planarization characteristics while fortifying heat resistance and etch resistance.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A monomer for a hardmask composition, the monomer being represented by one of the following Chemical Formulae A to D:

[Chemical Formula A]

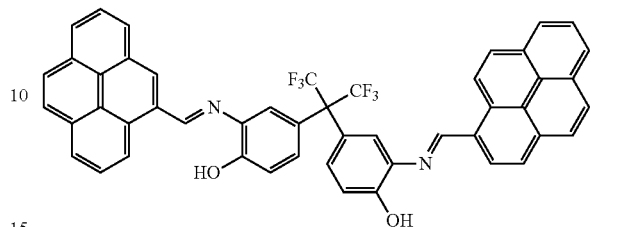

[Chemical Formula B]

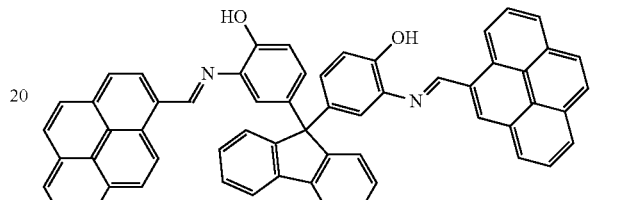

[Chemical Formula C]

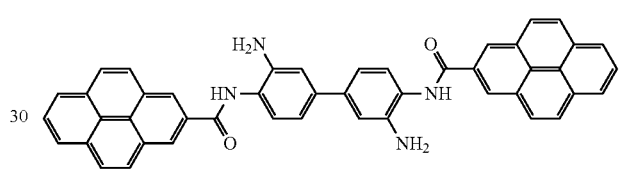

[Chemical Formula D]

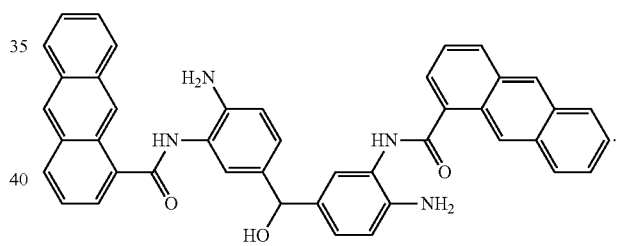

2. A hardmask composition, comprising:
a solvent; and
a monomer represented by the following Chemical Formula 1:

[Chemical Formula 1]

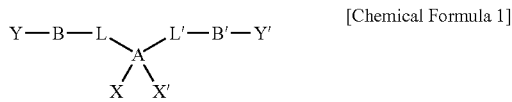

wherein, in Chemical Formula 1,
A, B, and B' are each independently a substituted aromatic ring-containing moiety,
L and L' are each independently —C(=O)NH—, or —C(H)=N—,
X and X' are each independently hydrogen, a hydroxy group, or an unsubstituted amino group, and
Y and Y' are each independently hydrogen,
wherein, when the hardmask composition is heat-treated at about 100 to about 500° C. for about 60 seconds to about 20 minutes, the monomer forms a structure represented by one of the following Chemical Formulae 6 to 9:

[Chemical Formula 6]

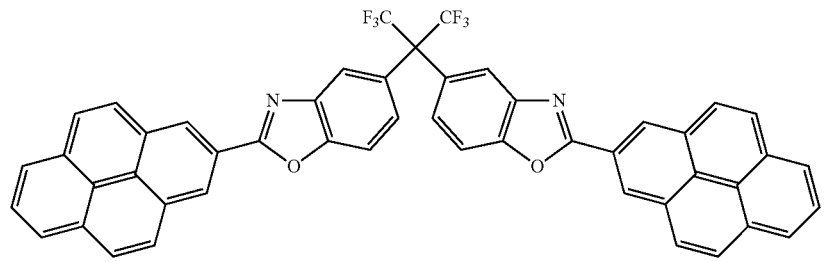

[Chemical Formula 7]

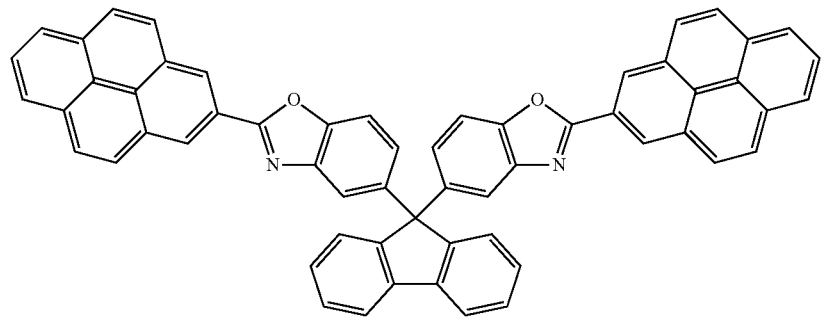

[Chemical Formula 8]

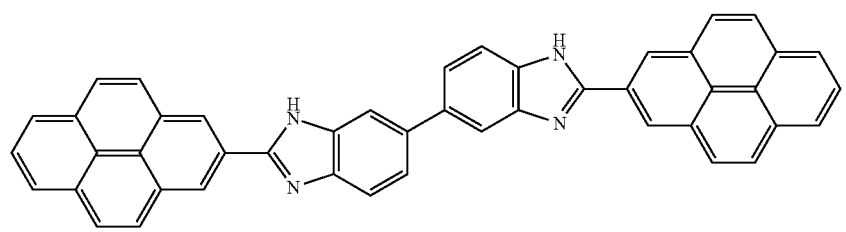

[Chemical Formula 9]

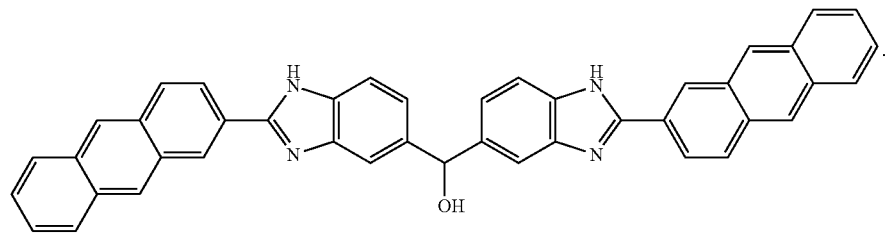

3. The hardmask composition as claimed in claim 1, wherein the monomer is included in the composition in an amount of about 0.1 wt % to about 30 wt %, based on a total weight of the hardmask composition.

4. A method of forming patterns, the method comprising:
providing a material layer on a substrate,
applying the hardmask composition as claimed in claim 1 on the material layer,
heat-treating the hardmask composition to form a hardmask layer,
forming a silicon-containing thin layer on the hardmask layer,
forming a photoresist layer on the silicon-containing thin layer,
exposing and developing the photoresist layer to form a photoresist pattern;
selectively removing the silicon-containing thin layer and the hardmask layer using the photoresist pattern to expose a part of the material layer, and
etching an exposed part of the material layer.

5. The method as claimed in claim 4, wherein applying the hardmask composition includes spin-on coating.

6. The method as claimed in claim 4, wherein heat-treating the hardmask composition to form the hardmask layer includes heat-treating at about 100° C. to about 500° C.

7. The method as claimed in claim 4, further comprising forming a bottom antireflective coating on the silicon-containing thin layer.

8. The method as claimed in claim 4, wherein the silicon-containing thin layer includes silicon oxynitride.

* * * * *